United States Patent
Odidi et al.

(10) Patent No.: US 10,960,077 B2
(45) Date of Patent: *Mar. 30, 2021

(54) ABUSE AND ALCOHOL RESISTANT DRUG COMPOSITION

(75) Inventors: Isa Odidi, Toronto (CA); Amina Odidi, Toronto (CA)

(73) Assignee: Intellipharmaceutics Corp., Ontario (CA)

(*) Notice: Subject to any disclaimer, the term of this patent is extended or adjusted under 35 U.S.C. 154(b) by 845 days.

This patent is subject to a terminal disclaimer.

(21) Appl. No.: 11/432,226

(22) Filed: May 12, 2006

(65) Prior Publication Data

US 2014/0010860 A1    Jan. 9, 2014

(51) Int. Cl.
- A61K 47/44    (2017.01)
- A61K 9/06    (2006.01)
- A61K 9/48    (2006.01)
- A61K 31/485    (2006.01)
- A61K 31/137    (2006.01)
- A61K 47/02    (2006.01)

(52) U.S. Cl.
CPC ............... *A61K 47/44* (2013.01); *A61K 9/06* (2013.01); *A61K 9/485* (2013.01); *A61K 9/4825* (2013.01); *A61K 9/4858* (2013.01); *A61K 9/4866* (2013.01); *A61K 9/4875* (2013.01); *A61K 9/4891* (2013.01); *A61K 31/137* (2013.01); *A61K 31/485* (2013.01); *A61K 47/02* (2013.01); *A61K 9/4808* (2013.01)

(58) Field of Classification Search
None
See application file for complete search history.

(56) References Cited

U.S. PATENT DOCUMENTS

| | | |
|---|---|---|
| 2,540,979 A | 2/1951 | MacDonnell |
| 3,254,088 A | 5/1966 | Juda et al. |
| 3,493,657 A | 2/1970 | Lewenstein |
| 3,629,393 A | 12/1971 | Nakamoto et al. |
| 3,728,445 A | 4/1973 | Bardani |
| 3,773,955 A | 11/1973 | Pachter |
| 3,789,117 A | 1/1974 | Tsujino |
| 3,819,706 A | 6/1974 | Mehta |
| 3,845,770 A | 11/1974 | Higuchi |
| 3,856,721 A | 12/1974 | Fritschel |
| 3,916,899 A | 11/1975 | Theeuwes et al. |
| 4,008,719 A | 2/1977 | Theeuwes |
| 4,016,880 A | 4/1977 | Theeuwes |
| 4,034,758 A | 7/1977 | Theeuwes |
| 4,036,228 A | 7/1977 | Theeuwes |
| 4,045,563 A | 8/1977 | Berntsson et al. |
| 4,060,598 A | 11/1977 | Groppenbacher et al. |
| 4,077,407 A | 3/1978 | Theeuwes |
| 4,160,452 A | 7/1979 | Theeuwes |
| 4,161,477 A | 7/1979 | Long |
| 4,183,838 A | 1/1980 | Gagliani |
| 4,183,839 A | 1/1980 | Gagliani |
| 4,193,985 A | 3/1980 | Bechgaard |
| 4,200,098 A | 4/1980 | Ayer |
| 4,218,433 A | 8/1980 | Kooichi et al. |
| 4,248,856 A | 2/1981 | Guley et al. |
| 4,250,136 A | 2/1981 | Rex |
| 4,252,786 A | 2/1981 | Weiss et al. |
| 4,255,431 A | 3/1981 | Junggren et al. |
| 4,309,405 A | 1/1982 | Guley et al. |
| 4,327,725 A | 5/1982 | Cortese |
| 4,330,338 A | 5/1982 | Banker |
| 4,337,257 A | 6/1982 | Junggren |
| 4,389,393 A | 6/1983 | Schor |
| 4,425,441 A | 1/1984 | Gagliani et al. |
| 4,457,933 A | 7/1984 | Gordon |
| 4,461,759 A | 7/1984 | Dunn |
| 4,486,412 A | 12/1984 | Shah et al. |
| 4,508,905 A | 4/1985 | Junggren |
| 4,514,538 A | 4/1985 | Shvakhman et al. |
| 4,517,112 A | 5/1985 | Mardis et al. |

(Continued)

FOREIGN PATENT DOCUMENTS

| | | |
|---|---|---|
| CA | 2286684 A1 | 10/1998 |
| CA | 2529984 A1 | 12/2004 |

(Continued)

OTHER PUBLICATIONS

Paste, http://www.thefreedictionary.com/paste, accessed Jun. 29, 2012.*
Paste, www.thefreedictionary.com/paste, accessed Jun. 26, 2012.*
Merriam-Webster Dictionay, "Paste", http://www.merriam-webster.com/dictionary/paste, accessed Dec. 16, 2014.*
International Search Report and Written Opinion for PCT/CA2007/000862; dated May 14, 2007.
Publication No. US2006/0039864; Publication Date—Feb. 23, 2006.
Publication No. US2007/0104778; Publication date—May 10, 2007.

(Continued)

Primary Examiner — Melissa L Fisher

(74) Attorney, Agent, or Firm — Thomas | Horstemeyer, LLP

(57) ABSTRACT

A liquid or semi-solid matrix or magma or paste which is non-newtonian, thixotropic and pseudoplastic and composed of one or more controlled release agent, and/or one or more clays such as bentonite and/or one or more fillers in a non aqueous vehicle, and optionally materials selected from disintegrants, humectants, surfactants and stabilizers. The composition and physicochemical properties makes it harder or prevents dose dumping of narcotic analgesics in the presence of alcohol and harder to abuse opiod agonists or narcotic analgesics and discourages drug abuse via crushing, milling or grinding the dosage form to powder or heating the dosage form to vapour and snorting or inhalation by the nasal route or dissolving to abuse via the parenteral route.

26 Claims, No Drawings

(56) References Cited

U.S. PATENT DOCUMENTS

| | | |
|---|---|---|
| 4,518,717 A | 5/1985 | Long et al. |
| 4,545,412 A | 10/1985 | Gamberini |
| 4,582,835 A | 4/1986 | Lewis |
| 4,606,909 A | 8/1986 | Bechgaard |
| 4,610,870 A | 9/1986 | Jain et al. |
| 4,612,008 A | 9/1986 | Wong et al. |
| 4,626,539 A * | 12/1986 | Aungst et al. ............... 514/282 |
| 4,628,098 A | 12/1986 | Nohara et al. |
| 4,666,705 A | 5/1987 | DeCrosta et al. |
| 4,676,929 A | 6/1987 | Rittler |
| 4,684,516 A | 8/1987 | Bhutani |
| 4,686,230 A | 8/1987 | Rainer et al. |
| 4,689,333 A | 8/1987 | Nohara et al. |
| 4,704,285 A | 11/1987 | Alderman |
| 4,708,834 A | 11/1987 | Cohen et al. |
| 4,713,248 A | 12/1987 | Kjornaes et al. |
| 4,723,958 A | 2/1988 | Pope et al. |
| 4,728,512 A | 3/1988 | Mehta |
| 4,756,911 A | 7/1988 | Drost et al. |
| 4,758,579 A | 7/1988 | Kohl et al. |
| 4,765,989 A | 8/1988 | Wong et al. |
| 4,783,337 A | 11/1988 | Wong et al. |
| 4,786,505 A | 11/1988 | Lovgren et al. |
| 4,812,446 A | 3/1989 | Brand |
| 4,818,760 A | 4/1989 | Binder et al. |
| 4,832,958 A | 5/1989 | Baudier et al. |
| 4,844,905 A | 7/1989 | Ichikawa et al. |
| 4,844,909 A | 7/1989 | Goldie |
| 4,845,118 A | 7/1989 | Lang et al. |
| 4,851,228 A | 7/1989 | Zentner et al. |
| 4,853,230 A | 8/1989 | Lovgren et al. |
| 4,869,908 A | 9/1989 | Kirschner et al. |
| 4,880,631 A | 11/1989 | Haslam |
| 4,886,668 A | 12/1989 | Haslam |
| 4,891,223 A | 1/1990 | Ambegaonkar et al. |
| 4,892,742 A | 1/1990 | Shah |
| 4,900,557 A | 2/1990 | Dell et al. |
| 4,904,476 A | 2/1990 | Mehta et al. |
| 4,927,640 A | 5/1990 | Dahlinder et al. |
| 4,935,243 A | 6/1990 | Borkan et al. |
| 4,940,587 A | 7/1990 | Jenkins et al. |
| 4,940,588 A | 7/1990 | Sparks et al. |
| 4,946,853 A | 8/1990 | Bannon et al. |
| 4,963,365 A | 10/1990 | Samejima et al. |
| 4,965,269 A | 10/1990 | Brandstrom et al. |
| 4,966,768 A | 10/1990 | Michelucci et al. |
| 5,000,962 A | 3/1991 | Sangekar et al. |
| 5,004,614 A | 4/1991 | Staniforth |
| 5,021,433 A | 6/1991 | Alminger et al. |
| 5,028,434 A | 7/1991 | Barclay et al. |
| 5,045,552 A | 9/1991 | Souda et al. |
| 5,049,394 A | 9/1991 | Howard et al. |
| 5,071,643 A | 12/1991 | Yu et al. |
| 5,073,384 A | 12/1991 | Valentine et al. |
| 5,077,051 A | 12/1991 | Gallopo |
| 5,123,146 A | 6/1992 | Olson |
| 5,149,702 A | 9/1992 | Yamada et al. |
| 5,190,763 A | 3/1993 | Edgren et al. |
| 5,202,128 A | 4/1993 | Morella et al. |
| 5,219,572 A | 6/1993 | Sivaramakrishnan |
| 5,229,131 A | 7/1993 | Amidon et al. |
| 5,236,714 A | 8/1993 | Lee et al. |
| 5,240,712 A | 8/1993 | Smith |
| 5,252,339 A | 10/1993 | Cristofori et al. |
| 5,260,069 A | 11/1993 | Chen |
| 5,286,497 A | 2/1994 | Hendrickson et al. |
| 5,288,500 A | 2/1994 | Ibsen |
| 5,290,816 A | 3/1994 | Blumberg |
| 5,300,291 A | 4/1994 | Sablotsky |
| 5,330,766 A | 7/1994 | Morella et al. |
| 5,376,388 A | 12/1994 | Meyers |
| 5,378,474 A | 1/1995 | Morella et al. |
| 5,393,528 A | 2/1995 | Staab |
| 5,415,871 A | 5/1995 | Pankhania et al. |
| 5,425,950 A | 6/1995 | Dandiker et al. |
| 5,430,042 A | 7/1995 | Lindberg et al. |
| 5,445,829 A | 8/1995 | Paradissis et al. |
| 5,458,887 A | 10/1995 | Chen et al. |
| 5,472,711 A | 12/1995 | Baichwal |
| 5,480,335 A | 1/1996 | Caveza |
| 5,503,846 A | 4/1996 | Wehling |
| 5,508,040 A | 4/1996 | Chen |
| 5,527,545 A | 6/1996 | Santus et al. |
| 5,595,762 A | 1/1997 | Derrieu |
| 5,681,581 A | 10/1997 | Dunn |
| 5,681,585 A | 10/1997 | Oshlack |
| 5,708,017 A | 1/1998 | Dave et al. |
| 5,713,000 A | 1/1998 | Larson |
| 5,736,159 A | 4/1998 | Chen et al. |
| 5,753,265 A | 5/1998 | Bergstrand |
| 5,759,577 A | 6/1998 | Barcomb |
| 5,760,121 A * | 6/1998 | Beall et al. ............... 524/450 |
| 5,780,055 A | 7/1998 | Habib et al. |
| 5,783,215 A | 7/1998 | Arwidsson et al. |
| 5,795,583 A | 8/1998 | Grune et al. |
| 5,800,422 A | 9/1998 | Dong et al. |
| 5,817,338 A | 10/1998 | Bergstrand |
| 5,840,329 A | 11/1998 | Bai |
| 5,840,910 A | 11/1998 | Souda |
| 5,879,708 A | 3/1999 | Makino et al. |
| 5,955,106 A | 9/1999 | Moeckel |
| 5,972,329 A | 10/1999 | Chuang et al. |
| 5,998,445 A | 12/1999 | Souda et al. |
| 6,022,562 A | 2/2000 | Autant et al. |
| 6,039,975 A | 3/2000 | Shah et al. |
| 6,046,177 A | 4/2000 | Stella et al. |
| 6,068,853 A | 5/2000 | Giannos et al. |
| 6,068,856 A | 5/2000 | Sachs |
| 6,090,401 A | 7/2000 | Gowan et al. |
| 6,099,859 A | 8/2000 | Cheng et al. |
| 6,106,864 A | 8/2000 | Dolan et al. |
| 6,183,776 B1 | 2/2001 | Depui et al. |
| 6,183,777 B1 | 2/2001 | Chen et al. |
| 6,194,001 B1 | 2/2001 | Gribbon et al. |
| 6,210,710 B1 | 4/2001 | Skinner |
| 6,228,400 B1 | 5/2001 | Lee et al. |
| 6,251,432 B1 | 6/2001 | Mazer et al. |
| 6,261,582 B1 * | 7/2001 | Needham et al. ............. 424/419 |
| 6,270,804 B1 | 8/2001 | Getz et al. |
| 6,296,876 B1 | 10/2001 | Odidi et al. |
| 6,312,723 B1 | 11/2001 | Whittle et al. |
| 6,312,724 B1 | 11/2001 | Odidi et al. |
| 6,368,635 B1 | 4/2002 | Akiyama et al. |
| 6,433,040 B1 | 8/2002 | Dellamary et al. |
| 6,479,075 B1 | 11/2002 | Odidi et al. |
| 6,489,346 B1 | 12/2002 | Phillips |
| 6,491,949 B2 | 12/2002 | Faour et al. |
| 6,509,037 B2 | 1/2003 | Odidi |
| 6,527,051 B1 | 3/2003 | Reddy et al. |
| 6,555,127 B2 * | 4/2003 | Steiner ..................... 424/439 |
| 6,558,704 B1 | 5/2003 | Bartholomaeus et al. |
| 6,569,453 B2 | 5/2003 | Linder et al. |
| 6,599,529 B1 | 7/2003 | Skinhoj |
| 6,605,300 B1 | 8/2003 | Burnside et al. |
| 6,607,751 B1 * | 8/2003 | Odidi et al. ............... 424/488 |
| 6,627,635 B2 | 9/2003 | Palermo et al. |
| 6,645,524 B2 | 11/2003 | Midha et al. |
| 6,645,528 B1 | 11/2003 | Straub et al. |
| 6,645,988 B2 | 11/2003 | Phillips |
| 6,652,882 B1 | 11/2003 | Odidi et al. |
| 6,673,367 B1 | 1/2004 | Goldenheim et al. |
| 6,676,966 B1 | 1/2004 | Odidi et al. |
| 6,696,088 B2 | 2/2004 | Oshlack et al. |
| 6,699,885 B2 | 3/2004 | Phillips |
| 6,780,882 B2 | 8/2004 | Phillips |
| 6,800,668 B1 | 10/2004 | Odidi et al. |
| 6,902,742 B2 | 6/2005 | Devane et al. |
| 6,911,217 B1 | 6/2005 | Gren et al. |
| 6,946,146 B2 | 9/2005 | Mulye |
| 6,991,804 B2 | 1/2006 | Helmus et al. |
| 7,090,867 B2 | 8/2006 | Odidi et al. |
| 7,135,465 B2 | 11/2006 | Abramowitz et al. |
| 7,157,103 B2 | 1/2007 | Sackler |
| 7,858,119 B1 | 12/2010 | Odidi et al. |

(56) References Cited

U.S. PATENT DOCUMENTS

| | | |
|---|---|---|
| 7,906,143 B1 | 3/2011 | Odidi et al. |
| 9,078,827 B2 | 7/2015 | Odidi |
| 2001/0006649 A1 | 7/2001 | Chen |
| 2002/0002147 A1 | 1/2002 | Abramowitz et al. |
| 2002/0045646 A1 | 4/2002 | Phillips |
| 2002/0086885 A1 | 7/2002 | Odaka et al. |
| 2002/0110590 A1 | 8/2002 | Shaked et al. |
| 2002/0128293 A1 | 9/2002 | Rampal et al. |
| 2002/0132005 A1 | 9/2002 | Faour |
| 2002/0150535 A1 | 10/2002 | Madras et al. |
| 2003/0064099 A1* | 4/2003 | Oshlack et al. ............ 424/465 |
| 2003/0064101 A1 | 4/2003 | Mehta et al. |
| 2003/0068370 A1* | 4/2003 | Sackler ................... 424/465 |
| 2003/0068371 A1 | 4/2003 | Oshlack et al. |
| 2003/0077297 A1 | 4/2003 | Chen et al. |
| 2003/0118641 A1 | 6/2003 | Maloney et al. |
| 2003/0118669 A1 | 6/2003 | Phillips |
| 2003/0185887 A1 | 10/2003 | Chen et al. |
| 2003/0215507 A1 | 11/2003 | Sherman et al. |
| 2003/0215527 A1 | 11/2003 | Phillips |
| 2003/0220413 A1 | 11/2003 | Petereit et al. |
| 2003/0235616 A1 | 12/2003 | Sowden et al. |
| 2004/0048896 A1 | 3/2004 | Phillips |
| 2004/0058018 A1 | 3/2004 | Phillips |
| 2004/0101558 A1 | 5/2004 | Dietrich et al. |
| 2004/0131669 A1 | 7/2004 | Kerc |
| 2004/0171646 A1 | 9/2004 | Phillips |
| 2004/0185093 A1 | 9/2004 | Szymczak |
| 2004/0198775 A1 | 10/2004 | Fraser et al. |
| 2004/0265370 A1 | 12/2004 | Odidi et al. |
| 2004/0265380 A1 | 12/2004 | Delmas et al. |
| 2005/0004171 A1 | 1/2005 | Phillips |
| 2005/0042304 A1 | 2/2005 | Phillips |
| 2005/0054682 A1 | 3/2005 | Phillips |
| 2005/0129778 A1 | 6/2005 | Mulye |
| 2005/0186268 A1 | 8/2005 | Hoshi et al. |
| 2005/0191349 A1 | 9/2005 | Boehm et al. |
| 2005/0196436 A1 | 9/2005 | Chantranukul et al. |
| 2005/0214373 A1 | 9/2005 | Desai et al. |
| 2006/0003001 A1 | 1/2006 | Devane et al. |
| 2006/0003007 A1 | 1/2006 | Odidi et al. |
| 2006/0004193 A1 | 1/2006 | Muller |
| 2006/0018948 A1 | 1/2006 | Guire et al. |
| 2006/0024361 A1 | 2/2006 | Odidi et al. |
| 2006/0039864 A1 | 2/2006 | Bartholomaus et al. |
| 2006/0039976 A1 | 2/2006 | Odidi et al. |
| 2006/0099246 A1 | 5/2006 | Tanner et al. |
| 2006/0017336 A1 | 6/2006 | Knauff |
| 2006/0153905 A1* | 7/2006 | Carrara et al. ................ 424/449 |
| 2006/0153909 A1 | 7/2006 | Motoune |
| 2006/0205681 A1 | 9/2006 | Moaddeb |
| 2007/0003619 A1 | 1/2007 | Smith |
| 2007/0009589 A1 | 1/2007 | Raghupathi et al. |
| 2007/0077293 A1 | 4/2007 | Park |
| 2007/0104778 A1 | 5/2007 | Zeng et al. |
| 2007/0131357 A1 | 6/2007 | Wu |
| 2007/0166370 A1 | 7/2007 | Odidi et al. |
| 2007/0286902 A1 | 12/2007 | Xie et al. |
| 2009/0220613 A1 | 9/2009 | Odidi et al. |

FOREIGN PATENT DOCUMENTS

| | | | |
|---|---|---|---|
| CA | 2551946 | 7/2005 | |
| CN | 1634116 A | 7/2005 | |
| DE | 1204363 | 8/1964 | |
| DE | 3531487 C2 | 8/1985 | |
| DE | 3943242 A1 | 6/1990 | |
| DE | 19635676 A1 | 3/1998 | |
| EP | 0005129 B1 | 4/1981 | |
| EP | 0157695 A2 | 9/1985 | |
| EP | 0166287 B1 | 1/1986 | |
| EP | 0174726 A1 | 3/1986 | |
| EP | 0184322 B1 | 6/1986 | |
| EP | 0234485 B1 | 9/1987 | |
| EP | 080341 B1 | 10/1987 | |
| EP | 0261478 A1 | 3/1988 | |
| EP | 0268956 B1 | 6/1988 | |
| EP | 0270305 A2 | 6/1988 | |
| EP | 0342522 A1 | 11/1989 | |
| EP | 0366321 A1 | 5/1990 | |
| EP | 0403383 A1 | 12/1990 | |
| EP | 0434999 B1 | 7/1991 | |
| EP | 0453001 A1 | 10/1991 | |
| EP | 0527638 A1 | 2/1993 | |
| EP | 0533790 B1 | 3/1993 | |
| EP | 0797991 A1 | 10/1997 | |
| EP | 0960620 A1 | 12/1999 | |
| EP | 1017370 B1 | 7/2000 | |
| EP | 1493435 | 1/2005 | |
| EP | 1731142 A1 | 12/2006 | |
| FR | 2419722 A1 | 1/1979 | |
| FR | 2624012 | 12/1987 | ............... A61K 9/48 |
| FR | 2624012 | 9/1989 | |
| FR | 2778848 | 11/1999 | |
| GB | 2134516 A | 8/1984 | |
| GB | 2163747 A | 3/1986 | |
| HU | 203477 | 10/1989 | ............... A61K 9/10 |
| HU | 203477 B | 1/1991 | |
| JP | 2002-068964 | 3/2002 | |
| JP | 2005500364 | 1/2005 | |
| WO | WO8503436 A1 | 8/1985 | |
| WO | WO8705212 A1 | 9/1987 | |
| WO | WO9011070 A1 | 10/1990 | |
| WO | WO 91/07950 | 11/1990 | ............... A61K 9/48 |
| WO | WO9107950 A1 | 6/1991 | |
| WO | WO9116885 A1 | 11/1991 | |
| WO | WO9119710 A1 | 12/1991 | |
| WO | WO9204013 A1 | 3/1992 | |
| WO | WO9208716 A1 | 5/1992 | |
| WO | WO9323770 A1 | 7/1993 | |
| WO | WO9428882 A1 | 12/1994 | |
| WO | WO9816206 A1 | 4/1998 | |
| WO | WO9851287 A1 | 11/1998 | |
| WO | WO9912524 A1 | 3/1999 | |
| WO | 02/30398 A2 | 4/2002 | |
| WO | 0230398 | 4/2002 | |
| WO | 0230398 A2 | 4/2002 | |
| WO | WO0230398 A2 | 4/2002 | |
| WO | 03013538 A1 | 2/2003 | |
| WO | 2003013476 A1 | 2/2003 | |
| WO | WO03009846 A1 | 2/2003 | |
| WO | 03086364 A1 | 10/2003 | |
| WO | WO04000825 A1 | 12/2003 | |
| WO | 200402418 A2 | 3/2004 | |
| WO | 2004024128 | 3/2004 | |
| WO | 2004050023 A2 | 6/2004 | |
| WO | 2004056354 A1 | 7/2004 | |
| WO | WO04056354 A1 | 7/2004 | |
| WO | 2005021009 A2 | 3/2005 | |
| WO | WO0137817 A1 | 3/2005 | |
| WO | 2005065661 A2 | 7/2005 | |
| WO | 2005097075 A2 | 10/2005 | |
| WO | 2005099674 A1 | 10/2005 | |
| WO | WO2005/097075 | * 10/2005 | |
| WO | 2006017336 A2 | 2/2006 | |
| WO | 2006085335 A2 | 8/2006 | |
| WO | 2007082770 A1 | 7/2007 | |
| WO | 2008122993 A1 | 10/2008 | |
| WO | 2009113061 A1 | 9/2009 | |
| WO | 2010044842 A1 | 4/2010 | |
| WO | 2012002644 A2 | 1/2012 | |

OTHER PUBLICATIONS

Sunshine, et al., "Analgesic Efficacy of Pentazocine Versus a Pentazocine-Naxloxone Combination Following Oral Administration", Clin. J. Pain, 1988: 4:35-40.

Wang, et al., "Crossover and Parallel Study of Oral Analgesics", J. Clin. Parmacl., 1981; 21:162-8.

Remington's Pharmaceutical Sciences, 18th ed. Chapter 83, pp. 1539-1540 (1990).

A. Banga et al., "Incorporation of Simethicone into Syrup or clear Base Liquid Orals", Drug Development and Industrial Pharmacy, 15(5), pp. 671-704 (1989).

(56) References Cited

OTHER PUBLICATIONS

Odidi, Office Action dated Mar. 12, 2010 for U.S. Appl. No. 12/092,654, filed May 5, 2008.
Odidi, International Search Report and Written Opinion dated Aug. 31, 2007 for PCT/CA2007/000862 filed May 14, 2007.
Odidi, International Preliminary Report on Patentability dated Nov. 27, 2008 for PCT/CA2007/000862 filed May 14, 2007.
Odidi, Office Action dated Nov. 25, 2009 for Canadian Patent Application No. 2,626,558 filed Jan. 2006.
Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.
Arora, S. et al, Pulsatie Drug Delivery Systems: An Approach for Controlled Drug Delivery, Indian J. Pharm. Sci., (2006), vol. 68, pp. 295-300.
Aulton, M. E.—The science of dosage form design, (1988), pp. 316-321, (Churchill Livingstone Ed.), Pharmaceutics.
Banga, A. et al., "Incorporation of Simethicone into Syrup or Clear Base Liquid Orals", Drug Development and Industrial Pharmacy, (1989), vol. 15(5), pp. 671-704.
Conner, A. L. et al., A Scintigraphic Study to Investigate the Potential for Altered Gut Distribution of Loperaminde from a Loperaminde-Simethicone Formation in Man, European Journal of Pharmaceutical Sciences, (2001), vol. 13, pp. 369-374.
Dashevsky, A. etal., pH-independent Release of Baisc Drug from Pellets Coated with the Extended Release Polymer Dispersion Kollicoat® SR 30 D and the Enteric Polymer Dispersion Kollicoat® MAE 30 DP, European Journal of Pharmaceutics and Biopharmaceuticals, (2004), vol. 58, pp. 45-49 (available online Jun. 1, 2004).
Deshpande, A. et al., Development of a Novel Controlled-Release System for Gastric Retention, Pharmaceutical Research, (1997), vol. 14, No. 6, pp. 815-819.
Krögel, I. et al., Floating of Pulsatile Drug Delivery Systems Based on Coated Efferescent Cores, International Journal of Pharmaceutics, (1999) vol. 187, pp. 175-184 anl.
Laizure, S. C. et al., Stability of Bupropion and its Major Metabolites in Human Plasma, Therapeutic Drug Monitoring (1985), vol. 7 (4); p. 447.
Lehmann, K. et al.,—Fast Disintegrating Controlled Release Tablets from Coated Particles—Drugs Made in Germany, (1994) vol. 37, No. 2, pp. 53-60.
Martindale, The Extra Pharmacopoeia, 30th Ed. (The Pharmaceutical Press, London 1993).
Rakur, G. et al., 2-((2-Pyridylm-ethyl) Sulfiny) Benzimidazoles: Acid Sensitive Suicide Inhibitors of the Proton Transport System in the Parietal Cell, Biochem Biophys. Res. Comm. (1985), vol. 128, No. 1, pp. 477-484.
Remington's Pharmaceutical Sciences, 18th ed, (1990), Chapter 83, pp. 1539-1540.
Sathe, P.M. et al, Drug Product Performance, In Vitro, Generic Drug Product Development, (2004), vol. 143, Chapter 8, pp. 187-209.
Steward, P.A. Review of Pharmaceutical Controlled Release Method and Devices, (1995) 12 pages.
Sungthongjeen, S. et al.,—Development of Pulsatile Release Tablets with Swelling and Rupturable Layers, Journal of Controlled Release, (2004), vol. 95, pp. 1147-1159.
Sunshine, et al., "Analgesic Efficacy of Pentazocine Versus a Pentazocine-Naxloxone Combination Following Oral Administration", Clin. J. Pain, (1988), vol. 4, pp. 35-40.
Venkatraman et al., Chapter 22, An overview of Controlled Release Systems, Handbook of Pharmaceutical Controlled release Technology by Donald Wise, Published, (2002) p. 443.
Walters, S. M., Influence of pH on Hydrolytic Decomposition of Dimethylpropion Hydrochloride: Stability Studies on Drug Substance and Tables using High-Performance Liquid Chromatograph, J. Pharma Science, (1980), vol. 69 (10), p. 1208.
Wang, R. et al., Crossover and Parallel Study of Oral Analgesics, J. Clin. Pharmacl., (1981) Vo. 21, pp. 162-168.

Merriam-Webster Online Dictionary, http://www.meriam-webster.com/dictionary/prevent, obtained online Feb. 18, 2008.
Merriam-Webster Online Dictionary, http://www.meriam-webster.com/dictionary/cure, obtained online Dec. 16, 2009.
European Patent Application No. 04 737 76.2-2112, Examination Report dated Nov. 18, 2009.
Office Action for U.S. Appl. No. 10/561,700 dated Dec. 27, 2007.
Office Action for U.S. Appl. No. 10/561,700 dated Mar. 18, 2008.
Office Action for U.S. Appl. No. 10/561,700 dated Apr. 17, 2009.
Office Action for U.S. Appl. No. 10/561,700 dated Sep. 3, 2009.
Office Action for U.S. Appl. No. 10/861,809 dated Sep. 28, 2009.
Office Action for U.S. Appl. No. 10/861,809 dated Nov. 26, 2008.
Office Action for U.S. Appl. No. 10/861,809 dated Nov. 13, 2007.
Office Action for U.S. Appl. No. 12/092,654 dated Mar. 12, 2010.
Office Action for Canadian Patent Application No. 2,626,558 dated Nov. 25, 2009.
English translation of Office Action dated Oct. 13, 2010 corresponding to Chinese Patent Application No. 200780019372.7.
International Search Report and Written Opinion; PCT/CA2007/000540.
International Search Report and Written Opinion; PCT/CA2007/000548.
International Search Report and Written Opinion; PCTCA2007/000550.
International Search Report and Written Opinion; PCT/CA2007/000862.
International Search Report and Written Opinion dated Aug. 31, 2007; PCT/CA2007/000862.
International Preliminary Report on Patentability dated Nov. 27, 2008; PCT/CA2007/000862.
International Preliminary Examination Report; PCT/CA2002/01360.
International Search Report; PCT/CA2002/01360.
International Search Report; PCT/CA2002/00054.
International Search Report and Written Opinion; PCT/CA2004/000825.
Encyclopaedia of Polymer Science and Technology; vol. 10 (1969); published by John Wiley & Sons.
U.S. Appl. No. 11/473,386.
U.S. Appl. No. 09/947,464.
U.S. Appl. No. 10/561,700.
U.S. Appl. No. 12/696,118.
U.S. Appl. No. 12/225,956.
U.S. Appl. No. 12/225,954.
U.S. Appl. No. 11/432,226.
U.S. Appl. No. 12/092,654.
U.S. Appl. No. 10/924,649.
U.S. Appl. No. 10/900,415.
U.S. Appl. No. 10/880,474.
U.S. Appl. No. 11/315,868.
Torpac, Capsul Size Chart, 2000, pp. 1-3.
Supplemental European Search Report Prepared by Miralles J. Gimenez dated Aug. 23, 2012.
Supplemental European Search Report Prepared by Antonio Raposo dated Aug. 2, 2012.
International Search Report from PCT/CA2013/000610; dated Sep. 18, 2013; Prepared by Nasreddine Slougui on Sep. 13, 2013.
Canadian Intellectual Property Office, Office Action dated Nov. 15, 2013 in CA application 2,579,382, 2 pages.
Canadian Intellectual Property Office, Office Action dated Dec. 4, 2013 in CA application 2,648,278, 3 pages.
European Patent Office, Examination Report dated Sep. 24, 2013 for EP application 07 719 478.5-1455, 6 pages.
Super Disintegrants: Characterization and Function (From European Examination Report of #3 above), 2007 by Informa Healthcare USA, Inc., 18 pages.
Ganesh Rasve, et al.; Pulsatile Drug Delivery System: Current Scenario; International Journal of Pharma and Bio Sciences; vol. 2 / Issue 3/ Jul.-Sep. 2011; 12 pages.
Shang-Tian Yang/ Yang-Ming :Lo and David B. Mint; "Xanthan Gun1 Fermentation by Xanthomonas campestris Immobolized in a Novel Centrifugal Fibrous~Bed Bioreactor"; Biotechno!. Prog. 1996,

(56) References Cited

OTHER PUBLICATIONS 12, 630-637; Department of Chemical Engineering, The Ohio State University, Columbus, Ohio 43210.
Office Action for European Patent Application No. 07719784.6 dated Jul. 6, 2018.
Canadian Examination Search Report, 50 rue Victoria, Place du Portage 1, Gatineau Quebec K1A OC9; dated Sep. 29, 2017. 4 pages, Application No. 2,648,278.
Buhse, Lucinda, et al. "Topical drug classification." international journal of pharmaceutics 295 (2005): 101-112.
Porro et al., "Efficacy of pantoprazole in the prevention of peptic ulcers, induced by non-steroidal anti-inflammatory drugs: a prospective, placebo-controlled, double-blind, parallel-group study", Digest Liver Dis 2000; 32: 201-208.
Zulfiker et al., "Formulation Development Using Maize Starch & Avicel PH101 as Disintegrating Agents and Their Effect on Physical Characteristics & In Vitro Release Profile." International Journal of Pharmaceutical Sciences and Research 2011, vol. 2(8), pp. 2136-2141.

* cited by examiner

ABUSE AND ALCOHOL RESISTANT DRUG COMPOSITION

FIELD OF THE INVENTION

This invention is in the field of a single or combinations of drugs for medicinal purposes, in particular, analgesic compositions for the treatment of pain and is more particularly concerned with three things; (1) the prevention of three particular types of drug abuse, i.e., the illicit use by snorting/ inhalation, parenteral administration, or crushing and oral ingestion of dosage forms intended for oral administration (2) the prevention of dose dumping in the presence of alcohol and (3) timed or extended release compositions in gelatin capsules which despite its pseudoplastic or thixotropic nature maintains its integrity sufficiently to perform its controlled release functions during transit in the GIT. The invention describes liquid or semi-solid matrix or magma or paste of narcotic analgesic compositions containing oily, waxy or fatty substances, clays and controlled release agents. Optionally nasal irritants may be included in the invention.

It was surprisingly discovered that narcotic analgesic compositions containing materials selected from oily, waxy or fatty substances, clays and controlled release agents discouraged abuse and made it harder to abuse by crushing, dissolving, heating to cause evaporation and snorting, "shooting" or inhalation. This is due to the physicochemical nature of the composition.

The pharmaceutically acceptable nasal irritants when present bring about nasal irritation and annoyance feeling when the composition is brought in contact with the nasal membrane. The irritant agent is not in amounts sufficient to precipitate allergic type reactions or immune response upon snorting.

It was also surprisingly discovered that in the present invention the narcotic agent is not easily soluble and immediately available upon crushing and attempt at dissolving it for intravenous injection or to get access to the total drug immediately upon oral ingestion of the crushed dosage form does not met with easy success.

It was unexpectedly discovered that the composition of the present invention prevents and makes it harder for dose dumping of opioid agonists or narcotic analgesics in the presence of alcohol or during co-ingestion of alcohol.

It will be appreciated that this invention can be variously described, e.g., as a means of preventing dose dumping (when co-ingested with alcohol) and drug abuse by route of administration, or as an improvement in the formulation and compounding of narcotic analgesics or abuse-able substances compositions. However, all based on the discovery that unique combinations of characteristics of various analgesics and materials selected from the group nasal irritants, clays, controlled release agents, oily, waxy or fatty substances can be utilized to provide valuable medicaments substantially free of dose dumping and any potential for illicit use specifically by administration via a means other than the intended oral route.

BACKGROUND OF THE INVENTION

Oral opioid formulations are not only being abused by the parenteral route, but also via the nasal route when the abuser snorts the crushed dosage form and via the oral route when the abuser orally administers the crushed dosage form in order to obtain instantaneous access to all the drug in the dosage form.

Another route of abuse which has become of serious concern is snorting of fine powder obtained from crushed opioid dosage form or the oral ingestion of finely crushed extended release oral dosage form in order to instantaneously obtain the benefit of the total opioid present in the slow release dosage form.

Another phenomenon that has become of concern regarding the use of extended release opioid analgesics is the discovery that they dose dump in the presence of alcohol and release all their content at once.

Applicants are of the opinion that the prior art neither teaches nor suggests that compositions of the instant invention can be effectively employed to overcome the problem of abuse of opioid agonist or abuse-able substances.

Applicants are also of the opinion that the prior art neither teaches nor suggests that compositions of the instant invention can be effectively employed to overcome the problem of dose dumping of opioid agonist or abuse-able substances in the presence of alcohol.

Drug abuse has almost become a way of life to a rapidly growing segment of the world population, especially in the United States and Canada. It has become the vogue of many of the younger generation to experiment with any type of drug that will produce an emotional, psychological, euphoric, depressive or generally psychedelic experience.

Those drugs most commonly employed for such illicit purposes include the barbiturates, lysergic acid diethylamide (LSD), mescaline, marijuana (tetrahydrocannabinol), strong analgetics (heroin, codeine, morphine, meperidine, propoxyphene [Darvon], methadone, dihydrocodeinone, pentazocine, hydromorphine and the like), the central nervous system stimulants (the amphetamines and the like) and some of the major and minor tranquilizers (the promazines, meprobamate, the diazepines, and the like). Most of these compounds are commonly used in medicine for the legitimate treatment of various conditions and therefore have a limited availability in our society. While these agents are a necessary part of modern medicine, it would be highly desirable (1) to produce new drugs that do not possess drug abuse potential or (2) to "denature" the old agents to prevent their illicit use. The pharmaceutical industry has been striving to achieve the first goal for many years but most regrettably has only achieved very moderate success. If one focuses on the strong analgesics, it becomes apparent that much effort and money has been expended to produce chemicals possessing good analgesic activity but little or no addictive liability. While good progress has been made as evidenced, for example, by the development of propoxyphene as a replacement for codeine and pentazocine as a replacement for morphine or meperidine, it is unfortunate that these compounds are still reported in the medical literature to be addictive and/or euphoric and subjected to abuse by crushing and dissolving and heating/evaporation of the drug composition to enable immediate access to the drug by swallowing, inhalation, snorting, "shooting" or parenteral administration. Furthermore, some of these agents have undesirable side effects, i.e., bad hallucinations, etc.

It is commonly known to the narcotic enforcement agencies and others in the medical trades that a substantial amount of the strong analgesics destined for legitimate medicinal use are diverted to illicit use through dishonest or careless handling. In many instances, these drugs are obtained by the addict or potential addict by theft or casual prescribing practice by the physician.

It is known from experience that the true narcotic addict must feed his habit by the crushing and/or dissolving and heating and/or evaporation of the drug composition to enable immediate access to the drug by swallowing, inhalation, snorting, "shooting" or parenteral route (mainlining) to obtain the maximum euphoric effect. The potential addict or thrill-seeker will also experiment in the same manner. Unfortunately, a substantial amount of the legitimate strong analgesics formulated in oral dosage form are diverted to illicit parenteral use, i.e., the type of abuse with which this invention is concerned. Since the oral dosage forms of these drugs diverted from legitimate channels must be easily crushed, dissolved and heated/evaporated in order to get a form in which it can be administered to produce the desired euphoria, it follows that if these oral dosage forms are in some way rendered difficult or impossible to crush, dissolve, heated/evaporate or extract and made unpleasant for abuse via swallowing, snorting, inhalation and "shooting" or parenteral use the addict or potential addict will be cut off from this particular supply of euphoric drugs. Obviously, oral activity must be retained if a useful medicament is to be provided.

Many interchangeable terms are commonly used to describe the psychic or physical dependence of people upon drugs. The term addiction is most commonly used when talking about the strong analgesics or opioid agonist or abuse-able substances. The strong analgesics or opioid agonist or abuse-able substances, in contrast to the weaker agents such as aspirin, acetaminophen, and the like, are employed in the relief of more severe pain. They usually produce a euphoric effect when crushed and swallowed, snorted and "shoot" parenterally. When taken as oral controlled release composition there is usually no significant euphoria.

Addiction can develop to the barbiturates and strong analgesic agents or opioid agonist or abuse-able substances, in the sense of the term "addiction" as defined by the Committee on Problems of Drug Dependence of The National Research Council, namely, a state of periodic or chronic intoxication, detrimental to the individual and to society, produced by the repeated administration of a drug, its characteristics are a compulsion to take the drug and to increase the dose, with the development of psychic and sometimes physical dependence on the effects of the drug, so that the development of means to continue the administration of the drug becomes an important motive in the addict's existence.

Addiction to narcotics or narcotic-like strong analgesics often occurs by the legitimate chronic oral or parenteral administration of these agents in the alleviation of deep pain. More commonly, however, addiction to these agents occurs when the psychologically unbalanced or thrill-seeking individual looking for an escape from the realities of life finds his escape in the euphoria produced by the oral or parenteral administration of strong analgesics or opioid agonist or abuse-able substances. Euphoria is generally defined as a feeling of well-being. Euphoria can be produced in many ways, e.g., an exhilarating experience, alcohol, stimulants, depressants, narcotics, etc. For the purpose of this disclosure, "euphoria" is defined as an abnormal state of well-being produced by the parenteral administration of strong analgesics. The terms or "abuse-able substances", "euphoric analgesics" and "strong analgesics," often called narcotic or narcotic-like analgesics or opioid agonist, are also defined herein as including those chemical agents which upon oral or parenteral administration are capable of maintaining or partially maintaining a known addict addicted to heroin or the like without substantial withdrawal symptoms. For the purpose of this disclosure, a "strong analgesic" can also be described as any analgesic agent whose analgesic, euphoric or dependence producing actions are negated by the parenteral administration of an opioid antagonist.

There has been a lot of concern with regards to the performance of extended release narcortics taught in prior art and currently commercialized. This is because the extended release or controlled release mechanism of current extended release opioid agonists using compositions and methods taught in the prior art is compromised and destroyed in the presence of alcohol leading to the loss of controlled release effects and complete release or dose dumping of its opioid content. The danger and economic consequences of dose dumping in the presence of alcohol for current controlled release narcotic analgesics was highlighted when in Jul. 14, 2005 Purdue Pharma voluntarily took its pain-relieving Palladone (hydromorphone hydrochloride) capsules off the market. The company took the action on July 13 following an FDA request to withdraw Palladone because of safety concerns. The FDA approved Palladone in September 2004. The drug was launched by Purdue Pharma in February 2005. Palladone was approved for the management of persistent, moderate-to-severe pain in patients requiring continuous, around-the-clock pain relief with a high-potency opioid for an extended period of time. An FDA news release stated that "serious and potentially fatal adverse reactions can occur when Palladone extended release capsules are taken together with alcohol. Hydromorphone is a narcotic analgesic; used to relieve pain and also to suppress cough.

According to the FDA news release, "Palladone is a once-a-day pain management drug containing a very potent narcotic. New data gathered from a company-sponsored study testing the potential effects of alcohol use shows that when Palladone is taken with alcohol the extended release mechanism is harmed which can lead to dose-dumping. The FDA described "Dose-dumping, as the rapid release of the drug's active ingredient into the bloodstream. The agency's news release pointed out that dose-dumping, even with a low dose of Palladone (12 milligrams), could lead to "serious, or even fatal, adverse events in some patients. The FDA also warned that the risk increases for higher doses of Palladone.

Health Canada also issued an Advisory to warn of serious health risks associated with the consumption of alcohol while taking any slow-release opioid analgesics, following data from Purdue Pharma.

It can be argued that just like in the case of Palladone all powerful pain management drugs such as opioid agonists or narcotic analgesics have serious risks if used incorrectly, and this is particularly true for the current extended release formulations in the prior art or under commercialization. In fact Health Canada has advised patients receiving other slow-release opioids to be aware that these products may react in a similar way to hydromorphone slow release formulation when co-ingested with alcohol i.e., they may be released into the blood quickly (dose-dumping) instead of over 24 hours.

This situation continues to present an unacceptably high level of patient risk. There is a great concern that as more patients take current compositions, safety problems will arise since even having one alcoholic drink could have fatal implications. The use of patient information vial label warnings regarding the dangers of using opioids and alcohol concomitantly is not expected to solve this problem. As a matter of fact the FDA has said that the agency doesn't believe that "potentially fatal, adverse events can be effectively managed by label warnings alone . . . ."

Health authorities have turned up the heat and are demanding the pharmaceutical companies come clean and put interests of patients first. Accordingly, to investigate if the same effect occurs with other slow-release drugs, Health Canada requests that all manufacturers of these products provide information on the interaction between their drug and alcohol; if this is not possible, studies investigating product interactions with alcohol are to be conducted and completed within six months. Health Canada states that the data will be assessed within a three-month period and that further action will be taken if required.

From the foregoing there is therefore an urgent and great need for compositions of opioid agonist or narcotic analgesics or abuse-able substances which are abuse resistant and or do not dose dump in the presence of alcohol.

Attempts have been made in the past to control the abuse potential associated with opioid analgesics. Parenteral dose of opioid analgesics are more potent as compared to the same dose administered orally. Therefore, drug abuse is often carried out by the extraction of the opioid from the dosage form, and the subsequent injection of the opioid (using any "suitable" vehicle for injection) in order to achieve a "high." Attempts to curtail abuse have therefore typically centered around the inclusion in the oral dosage form of an opioid antagonist which is not orally active but which will substantially block the analgesic effects of the opioid if one attempts to dissolve the opioid and administer it parenterally.

U.S. Pat. No. 3,254,088, describes the preparation of naloxone and its activity as a narcotic antagonist.

U.S. Pat. No. 3,493,657, describes the combination of morphine and naloxone as a composition for parenteral use "which has a strong analgesic, as well as antagonistic effect, without the occurrence of undesired or dangerous side effects."

A New York Times article appearing in a Jul. 14, 1970 issue described the oral administration of naloxone to narcotic addicts as a method of treatment. The oral administration of naloxone (in high doses) "makes it impossible for the addict to experience a high no matter how much heroin he uses."

The combination of pentazocine and naloxone has been utilized in tablets available in the United States, commercially available as TalwinB from Sanofi-Winthrop. TalwinB contains pentazocine hydrochloride equivalent to 50 mg base and naloxone hydrochloride equivalent to 0.5 mg base. TalwinB is indicated for the relief of moderate to severe pain. The amount of naloxone present in this combination has no action when taken orally, and will not interfere with the pharmacologic action of pentazocine. However, this amount of naloxone given by injection has profound antagonistic action to narcotic analgesics. Thus, the inclusion of naloxone is intended to curb a form of abuse of oral pentazocine which occurs when the dosage form is solubilized and injected. Therefore, this dosage has lower potential for parenteral abuse than previous oral pentazocine formulations. However, it is still subject to patient misuse and abuse by the oral route, for example, by the patient taking multiple doses at once.

Sunshine, et al. "Analgesic Efficacy of Pentazocine Versus a Pentazocine-Naloxone Combination Following Oral Administration", Clin. J. Pain, 1988:4:35-40, reported on the effect of the addition of 0.5 mg naloxone on the analgesic efficacy of pentazocine 50 mg. The combination was found to be significantly less efficacious than pentazocine for the sum of the pain intensity difference (SPID), and for relief and pain intensity difference (PID) at the fourth hour. For patients with moderate baseline pain, the combination produced significantly less pain relief than pentazocine for SPID and for relief and PID at hours 3 and 4. In patients with severe baseline pain, there was no significant difference found between pentazocine and the combination of pentazocine plus naloxone.

Wang, et al. "Crossover and Parallel Study of Oral Analgesics", J. Clin. Pharmaco.l 198 1; 21:162-8, studied the combination of naloxone 0.25 mg and PercodanB (composed of 4.5 mg oxycodone HC1, oxycodone terephthalate 0.28 mg, aspirin 224 mg, phenacetin 160 mg, and caffeine 32 mg) compared to PercodanB alone, and placebo in a crossover study of patients with chronic pain. The combination had lower mean scores than PercodanB alone for most of the analgesic hourly parameters in the later hours of the trial. However, for the summary variables, the combination showed no significant difference from either placebo or PercodanB.

A fixed combination of buprenorphine and naloxone was introduced in 1991 in New Zealand (TemgesicB, Reckitt & Colman) for the treatment of pain.

A fixed combination therapy comprising tilidine (50 mg) and naloxone (4 mg) has been available in Germany for the management of severe pain since 1978 (ValoronB, Goedecke). The rationale for the combination of these drugs is effective pain relief and the prevention of tilidine addiction through naloxone-induced antagonisms at the morphine receptor.

U.S. Pat. No. 3,773,955 (Pachter, et al.) described orally effective analgesic compositions which upon parenteral administration do not produce analgesia, euphoria, or physical dependence, and thereby prevent parenteral abuse of the analgetic agents. Such compositions contained from about 0.1 mg to about 10 mg naloxone per analgetic oral dose. This reference was not concerned with oral abuse of opioids.

U.S. Pat. No. 3,493,657 (Lewenstein, et al.) described compositions comprising naloxone and morphine or oxymorphone, which compositions were said to provide a strong analgesic effect without the occurrence of undesired side effects such as hallucinations.

U.S. Pat. No. 4,457,933 (Gordon, et al.) described a method for decreasing both the oral and parenteral abuse potential of strong analgetic agents such as oxycodone, propoxyphene and pentazocine, by combining an analgesic dose of the opioid with naloxone in a specific, relatively narrow range. Oxycodone-naloxone compositions having a ratio of 2.5-5:1 parts by weight and pentazocine-naloxone compositions having a ratio of 16-50:1 parts by weight were preferred. The dose of naloxone which was to be combined with the opioid is stated to substantially eliminate the possibility of either oral or parenteral abuse of the opioid without substantially affecting the oral analgesic activity thereof.

U.S. Pat. No. 4,582,835 (Lewis) describes a method of treating pain by administering a sublingually effective dose of buprenorphine with naloxone. Lewis describes dosage ratios of naloxone to buprenorphine from 1:3 to 1:1 for parenteral administration, and from 1:2 to 2:1 for sublingual administration.

U.S. Pat. No. 6,627,635 teaches a method of preventing abuse of opioid dosage forms wherein an analgesically effective amount of an orally active opioid agonist is combined with an opioid antagonist into an oral dosage form which would require at least a two-step extraction process to be separated from the opioid agonist, the amount of opioid antagonist including being sufficient to counteract opioid effects if extracted together with the opioid agonist and administered parenterally.

U.S. Pat. No. 6,696,088 discloses tamper-resistant oral opioid agonist formulations comprising (i) an opioid agonist in releasable form and (ii) a sequestered opioid antagonist which is substantially not released when the dosage form is administered intact, such that the ratio of the amount of antagonist released from said dosage form after tampering to the amount of said antagonist released from said intact dosage form is about 4:1 or greater, wherein said agonist and antagonist are interdispersed and are not isolated from each other in two distinct layers.

Despite all the above attempts in the prior art to address the problem of drug abuse, the problem persists partly because of design faults in the compositions and the addicts coming up with creative ways to beat the anti drug abuse mechanism. As at today the problem is escalating with at an alarming rate with devastating financial and social consequences.

To the best of our knowledge, the prior art neither teaches nor suggests that compositions of the instant invention can be effectively employed simultaneously to reduce the problem of, or discourage or make it difficult for drug abuse via snorting (nasal), oral or parenteral administration of crushed oral dosage formulations and that compositions of the instant invention when taken orally in the ordinary course, the irritant, sequestering agent and narcotic antagonist have no significant effect and do not block the therapeutic effect of the opioid analgesic.

The current invention makes use of compositions in gelatin capsules particularly hard gelatin capsules. The following information discloses the use of soft gelatin capsules as carriers for drugs in the prior art. However these do not teach the composition of the current invention The fill material used in a soft gelatin capsule generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a C.2-C.sub.5 polyol, such as propylene glycol or glycerin. The carrier forms a stable dispersion of the antacid salt and coats the antacid particles, thereby rendering them nonreactive with the soft gelatin capsule wall. The dispersion may also contain a polysiloxane flatulence-relieving agent, such as sirnethicone, as an optional ingredient. Such optional ingredients comprise about 0-5% by weight of the total dispersion.

U.S. Pat. No. 4,708,834 to Cohen et al. suggests a controlled release pharmaceutical dosage form comprising a soft gelatin capsule that encloses a water soluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, C.sub.2-C.sub.4 polyols and mixtures thereof.

U.S. Pat. No. 5,071,643 to M. Yu et al. also discusses the use of polyethylene glycols (PEG) as a fill material in soft gelatin dosage forms. PEGS having an average molecular weight between 400-600 are preferred for liquid fills, between 800-10,000 for semi-solid fills and between 10,000-100,000 for solid fills.

Remington's Pharmaceutical Sciences, 18th ed, Chapter 83, pp. 1539-40 (1990), reports that gelling agents used to make gels for pharmaceutical and cosmetic products, include sodium alginate and triethanolamine.

PCT Publication No. WO 91107950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600-4000. This gel fill cannot be expelled with a syringe at ambient temperature and therefore avoids the reported abuse of liquid filled capsules by intravenous drug abusers.

Antiflatulents are typically incorporated into compressible tablets by mixing the oily-like substances, such as simethicone, with standard tableting excipients prior to tableting. U.S. Pat. No. 5,073,384 to Valentine et al. describes a composition suitable for tableting comprising simethicone and a water soluble, maltodextrin agglomerate. The resulting combinate is reported to be free flowing and possess defoaming activity.

Hungarian Patent No. 203,477, published Jan. 28, 1991, describes an antiflatulent, solid dispersion containing poly (dimethylsiloxane) as a dispersed phase in a water soluble carrier. The dispersion also contains a lattice-forming and/or a crosslinking, viscosity-increasing macromolecular auxiliary substance such as polyvinyl chloride, polyacrylic acid, or polyvinylpyrrolidone and/or inorganic solidifying agent, such as tricalcium phosphate, calcium sulfate hemihydrate or calcium hydrogen phosphate. Example 1 reports a solid mass containing 60 g of polyethylene glycol 6000, 15 g of polyvinyl chloride and 25 g of activated dimethicone (simethicone) that can be ground and filled into solid gelatin capsules or made into tablets.

French Patent Application No. 2,624,012, published Jun. 9, 1989, relates to a soft gelatin capsule containing a suspension or solution of chloral hydrate in a high viscosity inert vehicle. Suitable vehicles for use in the capsule include oily solvents of mineral or vegetable oil, such as olive oil, peanut oil, paraffin oil, vaseline oil or mixtures of several oils; a liquid silicone such as dimethicone or simethicone; a glycol polymer such as polyethylene glycol 600, 800 or 1200; and a glycol such as ethylene glycol, propylene glycol or glycerol.

Simethicone has been incorporated in syrup or clear base liquid oral formulations. A. Banga et al. in "Incorporation of Simethicone into Syrup or Clear Base Liquid Orals," Drug Development and Industrial Pharmacy, 15(5), pgs. 691-704 (1989) describes a variety of vehicles for simethicone, but reports the best results were obtained with neutralized CARBOPOL™ (carboxypolymethylene) resins in combination with glycerin and propylene glycol.

U.S. Pat. No. 4,514,538 teach a self-sustaining waterproofing composition prepared by a method comprising mixing at least 75 parts of solvent wetted bentonite with (A) a material selected from the group consisting of dialkylphthalate, dialkyloxalate, sucrose acetate isobutyrate, glycerine and mixtures thereof, (B) said solvent being substantially unreactive with said bentonite and containing from about 30 to 50 parts benzene, and (C) a material selected from the group consisting of polyalkylmethacrylate, cellulose acetate, polyvinylalcohol, polyvinylbutyral, and mixtures thereof. This invention relates to compositions useful in the construction industry useful in waterproofing a structure.

U.S. Pat. No. 4,517,112 teaches Modified organophilic clay complexes, their preparation and non-aqueous systems containing them and more especially, organophilic organic-clay complexes which are dispersible in organic liquids to form a gel therein, which comprises the reaction product of (a) a smectite-type clay having a cation exchange capacity of at least 75 milliequivalents per 100 grams of said clay; (b) a primary anion selected from the group consisting of anions derived from organic sulfonic acids, alkylsulfates and mixtures thereof containing at least one lineal or branched alkyl group having greater than 9 carbon atoms, aromatic sulfonic acids and mixtures thereof; (c) a secondary anion different from said primary anion and selected from the group consisting of anions derived from organic acids having a pKa of less than about 11.0 and mixtures thereof; and (d) an organic cation is an amount sufficient to satisfy the cation in exchange capacity of said clay and the cationic activity of the primary and secondary anions wherein the resulting organic cation-organic anion complexes are intercalated with the smectite-type clay and wherein the combination of said primary and secondary anion synergistically increases the ease of dispersion of said organophilic clay gellant in an organic liquid. This invention relates to compositions gels which may be useful as lubricating greases, oil base muds, oil base packer fluids, paint-varnish-lacquer removers, paints, foundry molding sand binders, adhesives and sealants, inks, polyester laminating resins, polyester gel coats, and the like.

U.S. Pat. No. 4,676,929 This invention is concerned with useful gels generated from expandable, hydrated sheet silicates, also known as lattice layered silicates, or phyllosilicates. It is also concerned with articles of manufacture produced by further treatment of such gels, and with methods of generating and treating the gels. The silicate minerals of interest include vermiculite, beidellite, nontronite, volchonskoite, saponite, stevensite, sauconite, pimelite, bentonite, montmorillonite, hectorite, the smectites, attapulgite, sepiolite, phlogopite and biopyrobole; i.e., in essence the entire genus of hydrated or hydratable phyllosilicates whether of natural or synthetic origin.

These do not teach compositions of opioid agonists in hard gelatin capsule that are difficult to abuse and that will not does dump in the presence of alcohol or on co-ingestion with alcohol.

To date, there has been no disclosure of the use of the composition of the present invention to prevent and or make it harder for dose dumping of opioid agonists or narcotic analgesics in the presence of alcohol or during co-ingestion of alcohol.

There has also been no disclosure of the use of the composition of the present invention to prevent or discouraged abuse and make it harder to abuse opioid analgesics, narcotic analgesics or abuse-able substances. Furthermore, there has also been no disclosure of the composition of the present invention.

SUMMARY OF THE INVENTION

This invention is concerned with the development of a potent, orally effective, but abuse resistant analgesic composition that has substantially reduced drug abuse potential and, more particularly, essentially no abuse potential.

The object of the invention are also achieved by the formulation of a composition comprising narcotic or narcotic-like, analgesic agent in oral liquid or semi-solid matrix, magma, or paste in a capsule and composed of materials selected from clays, controlled release agents and oily, waxy or fatty substances in an amount and ratios which is sufficient to prevent the compromising or loss of integrity of the controlled release mechanism of the composition upon oral administration or co-ingestion with alcohol.

Another aspect of the invention is to provide a means to discourage three particular types of drug abuse, i.e., the illicit use by snorting/inhalation, parenteral administration, or crushing and oral ingestion of dosage forms intended for oral administration over 12 or 24 hours in order to rapidly release or make available the abuse-able agent.

Another objective achieved by this invention is the provision of a means for preventing dose dumping in the presence of alcohol and the prevention of the abuse of oral formulations of therapeutically valuable strong analgesics or opioid analgesics by the improvement in formulating such medicaments which comprises admixing therewith a balanced amount of opioid analgesic and materials selected from clays, oily, waxy or fatty substances and controlled release agents.

It is another object of this invention to provide a controlled release product and method in which the physicochemical nature of the composition helps to prevent dose dumping in the presence of alcohol and also discourage abuse and make it harder to abuse by crushing, milling or grinding and dissolving, heating to cause evaporation and snorting, "shooting" or inhalation.

It is yet another object of this invention to provide a composition in which the presence of pharmaceutically acceptable nasal irritants in sufficient amount to bring about nasal irritation and present an annoyance feeling (but not allergic type reactions or immune response) when the composition is brought in contact with the nasal membrane and hence discourage drug abuse via snorting or inhalation.

Yet another objective achieved by this invention is the provision of a means for preventing dose dumping of opioid analgesics in the presence of alcohol A further object of this invention is to provide high dose loading of opioid analgesic in a liquid or semi-solid matrix, magma or paste in a hard gelatin capsule.

A still further object of this invention is to provide a stable composition of opioid analgesic in a liquid or semi-solid matrix, magma or paste which does not interact with or compromise the integrity of the hard gelatin capsule Another objective of this invention is Compositions containing pharmaceutical active substances and materials selected from the group clays, controlled release agents, oily, waxy, and fatty substances for preventing dose dumping in the presence of alcohol and which makes it difficult for drug abuse A still further object of this invention is to provide a stable composition of opioid analgesic in a liquid or semi-solid matrix, magma or paste in hard gelatin capsule in which dissolution using a USP dissolution tester is not significantly different by the rotation speed of the basket or paddle in the speed range from about 25 rpm to about 150 rpm, or at about 50 rpm and about 100 rpm or at about 50 rpm and about 75 rpm or at about 100 rpm and about 150 rpm. The rotation speed does not interact with or compromise the integrity of the composition and release mechanism. Compositions that meet these requirements perform consistently in the GIT without fear of collapse or disintegration. They are not perturbed, crushed or damaged by GIT content, resident time or motility. These types of composition will be more reliable and highly prized.

A further objective of this invention is to provide compositions of the active substances, clays, controlled release agents and oily, waxy or fatty substances that are compatible with the gelatin capsule shell and not compromise the integrity of the capsule shell Another objective is to provide compositions of the active substances, clays, controlled release agents and oily, waxy or fatty substances in a gelatin capsule and applying a pH or non pH sensitive film coat to the internal and or external surface of the gelatin capsule in other to control the site and or rate of delivery of the active substances or protect the composition from environmental factors such as moisture or for aesthetic appeal.

The concentration of controlled release agents in the invention may be from about 2% to about 90% while the concentration of the oily substance may be from about 3% to about 99%. The concentration of the waxy or fatty substance may be from about 0.5% to about 70%. The concentration of clays in the invention is from about 0.1% to about 95%.

According to the method of treatment embodiment of the invention, a medical condition or dose dumping is sought to be prevented or treated by administering to a patient a pharmaceutical composition, as described above, comprising a narcotic analgesic and clays, controlled release agent and oily, waxy or fatty substances wherein the quantity and combination of materials in the composition is sufficient to form a liquid or semi solid matrix, paste or magma.

In a preferred composition, the particle size of non dissolved materials should be less than 1000 microns and the composition maintains its consistency/viscosity and homogeneity at room temperature conditions and during storage. A more preferred composition is a homogeneous non Newtonian, thixotropic or pseudoplastic paste or liquid/semi solid matrix.

In yet another preferred composition and method of application and manufacture of the embodiment of the invention, a controlled release composition may be filled into a gelatin capsule or dispensing device alone and utilized. Or it may be co-filled with non controlled release composition containing opioid antagonist and or immediate release non-narcotic analgesics or other pharmaceutically active substances. Such compositions allow for a clean break during formation or dosing ("stringing") into gelatin capsule or device. The right viscosity is critical. If the viscosity is too low splashing of the bushings may occur which could contaminate the area of overlap between the capsule body and cap and prevent a good seal from being formed. The present invention prevents the above mentioned problems.

The formulation may also be in the form of a solid. The means and area of application will depend on the particular condition that is being treated. It may be taken orally, implanted, intravenously or as a depot. It may be targeted at specific sites in the gastrointestinal tract (GIT) or to specific organs. It may be applied buccally and transdermally in a pouch or patch. The composition may be applied to bodies of water, such as rivers, lakes, or oceans, to the atmosphere, or to land. It is evident that the physical state of the formulation and the particular method of application may vary accordingly.

In a preferred method and composition the administration in man or animal may be internal, such as oral or parenteral. Such internal parenteral administration includes but is not limited to intravascular, intramuscular, subcutaneous, intradermal, intrathecal, and intracavitary routes of administration, as well as application to the external surface of an internal bodily organ, such as during a surgical or laparoscopic procedure. The administration may be topical, including administration to the skin or to a mucosal surface, including the oral, vaginal, rectal surfaces, to the surface of the eye, to the nasal passages, or to the ear canal.

The manufacture of the composition of this invention is relatively simple. Formulation is prepared at room temperature. Typically, no heating of the ingredients are required. However, when materials that are solid at room temperature are to be used, heating may be necessary. For this invention, solvent having high volatile properties are not preferred. Examples of such volatile solvents are: benzene, toluene, xylene, hexane, cyclohexanole, cyclohexane, methylcyclohexanole, dioxane, ethylacetate, acetone, amylacetate, propylacetate, methylethylketone, ethylcellosolve, isopropylalcohol, methanol, ethylalcohol and isoarnylalcohol.

DETAILED DESCRIPTION OF THE INVENTION

Examples of some of the opioid agonists or narcotic analgesics contemplated for use in this invention include alfentanil, allylprodine, alphaprodine, anileridine, benzylmorphine, bezitramide, buprenorphine, butorphanol, clonitazene, codeine, desomorphine, dextromoramide, dezocine, diampromide, diarnorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tramadol, tilidine, alphaprodine, dextroporpoxyphene, propiram, profadol, phenampromide, thiambutene, pholcodeine, 3-trans-dimethylamino-4-phenyl-4-trans-carbethoxy-.DELTA.'-cyclohexene, 3-dimethylamino-0-(4-methoxyphenylcarbamoyl)-propiophenone oxime, (−).beta.-2'-hydroxy-2,9-dimethyl-5-phenyl-6,7-benzomorphan, (−)2'-hydroxy-2-(3-methyl-2-butenyl)-9-methyl-5-phenyl-6,7-benzomorphan, pirinitramide, (−).alpha.-5,9-diethyl-2'-hydroxy-2-methyl-6,7-benzomorphan, ethyl 1-(2-dimethylaminoethyl)-4,5,6,7-tetrahydro-3-methyl-4-0x0-6-phenylindole-2-carboxylate, 1-Benzoylmethyl-2,3-dimethyl-3-(m-hydroxyphenyl)-piperidine, N-allyl7. alpha.-(1-(R)-hydroxy-1-methylbutyl)-6,14-endo-ethanotetrahydron ororipavine, (−)2'-hydroxy-2-methyl-6,7-benzomorphanno,r acylmethadol, phenoperidine, .alpha.-dl-methadol, .beta.-dl-methadol, .alpha.-1-methadol (2-15 mg), .beta.-dl-acetylmethadol, .alpha.-dl-acetylmethadol and beta-dl-acetylmethadol and pharmaceutically acceptable salts thereof, stereoisomers thereof, ethers thereof, esters thereof, and mixtures thereof.

The compositions of the instant invention can also contain other active ingredients. These include amongst others for example, opioid antagonists (such as naloxone), aspirin, phenacetin, caffeine, acetaminophen, antihistamines, homatropine methylbromide, phenyltoloxamine citrate, barbiturates, or the like, or multiple combinations thereof. Also included within the scope of the present invention are those compositions comprising narcotic analgesics in combination with non narcotic analgesics, antitussive preparations which contain narcotic or narcotic-like cough suppressants such as codeine, dihyrocodeinone, pholcodeine, and the like. Other products comprising a narcotic or narcotic-like composition for use as an antispasmotic in the gastro-intestinal tract, such as Camphorated Opium Tincture, U.S.P., Opium Tincture, U.S.P., Opium extract, N.F., and the like are to be considered an integral part of this invention.

Included in the compositions of this invention would be drugs most commonly employed for illicit purposes (to bring about a "high", euphoria, excitement, stupor, sleep deprivation etc.,) such as the barbiturates, lysergic acid diethylamide (LSD), mescaline, marijuana (tetrahydrocannabinol), heroin, and the like, the central nervous system stimulants (the amphetamines and the like) sedative, hypnotics and some of the major and minor tranquilizers (the promazines, meprobamate, the diazepines, and the like)

Examples of clays suitable for use in this invention are bentonite, veegum and other clay minerals such as phyllosilicates (Smectite, illite, sepiolite, palygorskite, muscovite, allevardite, amesite, hectorite, fluorohectorite, saponite, beidellite, talc, nontronite, stevensite, mica, vermiculite, fluorovermiculite, halloysite and fluorine-containing synthetic types of mica, phyllosilicates, beidellite; volkonskoite; hectorite; sauconite; sobockite; svinfordite; and the like. Other usehl materials include micaceous minerals, such as mixed illite/smectite minerals, such as rectorite, tarosovite, ledikite and admixtures of illites with the clay minerals named above. A swelling bentonite is preferred.

Oily, fatty and waxy components are a preferred embodiment of the current invention. These include oils and fats, waxes, hydrocarbons, higher fatty acids, higher alcohols, esters, metal salts of higher fatty acids, and the like. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated corn oil, hydrogenated rape seed oil, hydrogenated castor oil, hydrogenated coconut oil, hydrogenated soybean oil, etc.; and the like. Of these hydrogenated oils are preferred as an oil component of the present invention. Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc.; and the like. Of these preferred are carnauba wax, white beeswax and yellow beeswax. Paraffin, petrolatum, microcrystalline wax, and the like, are given as specific examples of hydrocarbons, with preferable hydrocarbons being paraffin and microcrystalline wax. Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid. Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like. Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydoxystearic triglyceride, etc.; and the like. Specific examples of metal salts of higher fatty acid are calcium stearate, magnesium stearate, aluminum stearate, zinc stearate, zinc palmitate, zinc myristate, magnesium myristate, and the like.

In a preferred embodiment the oils used in the invention are one or more selected from Almond Oil, Apricot Kernel Oil, Avocado Oil, Black Currant Oil, 14% GLA, Borage Oil, 20% GLA, Canola Oil, Carrot Oil, Castor Oil, Clove Leaf Oil, Coconut Oil, Corn Oil, Cottonseed Oil, Evening Primrose Oil, 9% GLA, Flaxseed Oil, 55% ALA, Grapeseed Oil, Hazelnut Oil, Hemp Oil, ALA/GLA, Hydrogenated Oils, Jojoba Oil, Golden Jojoba Oil, Water-white Kukui Nut Oil, Macadamia Nut Oil, Oat Oil, Olive Oil, Extra Virgin Olive Oil Pomace/"B" grade, Olive Oil, Pure/NF, Palm Oil, Parsley Seed Oil, Peach Kernel Oil, Peanut Oil, Pecan Oil, Pistachio Oil, Pumpkinseed Oil, Rice Bran Oil, Rose Hip Seed Oil, Rosemary Oil, Safflower Oil, Linoleic' Safflower Oil, High-Oleic, Sesame Oil NF, Sesame Oil Toasted, Soybean Oil, Sunflower Oil, Salad Sunflower Oil High-Oleic, Tea Tree Oil, Vegetable, Glycerine, USP, Walnut Oil, Wheat Germ Oil, Cold-pressed and mineral oil or other similar oils.

Controlled release agents that may be used in the composition of this invention include naturally occurring or synthetic, anionic or nonionic, hydrophobic, hydrophilic rubbers, polymers, starch derivatives, cellulose derivatives, polysaccharides, carbomer, reseins, acrylics, proteins, vinylpyrrolidone-vinyl-acetate-copolymers, glactomannan and galactomannan derivatives, carrageenans and the like. Specific examples are acacia, tragacanth, Xanthan gum, locust bean gum, guar-gum, karaya gum, pectin, arginic acid, polyethylene oxide, polyethylene glycol, propylene glycol arginate, hydroxypropyl methylcellulose, methylcellulose, hydroxypropyl cellulose, hydroxyethyl cellulose, carboxymethylcellulose sodium, polyvinylpyrrolidone, carboxyvinyl polymer, sodium polyacrylate, alpha starch, sodium carboxyrnethyl starch, albumin, dextrin, dextran sulfate, agar, gelatin, casein, sodium casein, pullulan, polyvinyl alcohol, deacetylated chitosan, polyethyoxazoline, poloxamers, ethylcellulose, chitin, chitosan, cellulose esters, aminoalkyl methacrylate polymer, anionic polymers of methacrylic acid and methacrylates, copolymers of acrylate and methacrylates with quaternary ammonium groups, ethylacrylate methylmethacrylate copolymers with a neutral ester group, polymethacrylates, surfactants, aliphatic polyesters, zein, polyvinyl acetate, polyvinyl chloride, and the like.

The following may be used in a preferred embodiment, a pharmaceutically acceptable acrylic polymer. Specific examples includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH independent or pH dependent.

Further examples of additives that may be used in the composition of the invention include, but are not limited to, ethyl lactate, phthalates such as dimethyl phthalate (DMP), diethyl phthalate (DEP), dibutyl phthalate (DBP), dioctyl phthalate, glycol ethers such as ethylene glycol diethyl ether, propylene glycol monomethyl ether, PPG-2 myristyl ether propionate, ethylene glycol monoethyl ether, diethylene glycol monoethyl ether, propylene glycol monotertiary butyl ether, dipropylene glycol monomethyl ether, N-methyl-2-pyrrolidone, 2 pyrrolidone, isopropyl myristate, isopropyl palmitate, octyl palmitate, dimethylacetamide, propylene glycol, propylene glycol monocaprylate, propylene glycol caprylatelcaprate, propylene glycol monolaurate, glycofurol, linoleic acid, linoeoyl macrogol-6 glycerides, oleic acid, oleic acid esters such as glyceryl dioleate, ethyl oleate, benzoic acid, oleoyl macrogol-6 glycerides, esters such as ethylbenzoate, benzylbenzoate, sucrose esters, sucrose acetate isobutyrate, esters of lactic acid, esters of oleic acid, sebacates such as dimethyl sebacate, diethyl sebacate, dibutyl sebacate, dipropylene glycol methyl ether acetate (DPM acetate), propylene carbonate, propylene glycol laurate, propylene glycol caprylatelcaprate, gamma butyrolactone, medium chain fatty acid triglycerides, glycerol and PEG esters of acids and fatty acids, PEG-6 glycerol mono oleate, PEG-6 glycerol linoleate, PEG-8 glycerol linoleate, caprylic acid esters such as caprylocapryl macrogol-8 glycerides, PEG-4 glyceryl caprylatelcaprate, PEG-8 glyceryl caprylatelcaprate, polyglyceryl-3-oleate, polyglyceryl-6-dioleate, polyglyceryl-3-isostearate, polyglyceryl polyoleate, decaglyceryl tetraoleate and glyceryl triacetate, glyceryl monooleate, glyceryl monolinoleate, dimethylformamide, dimethylsulfoxide, tetrahydrofuran, caprolactam, decylmethylsulfoxide, and, 1-dodecylazacycloheptan-2-one. The invention may contain surface active agents with varying hydrophilic lipophilic balance (HLB) values such as polyoxyethylene castor oil, polyoxyethylene hydrogenated castor oil, polyoxyethylene sorbitan fatty acid esters, polyoxyethylene alkyl esters, polyoxyethylene alkyl ethers, polyoxyethylene glycerol esters, sorbitan fatty acid esters, and sodium lauryl sulphate.

The antioxidants that may be used in this invention is selected from ascorbic acid, fbmaric acid, malic acid, alpha tocopherol, ascorbic acid palmitate, butylated hydroxyanisole, propyl gallate, sodium ascobate, and sodium metabisulfite or other suitable antioxidants and stabilizers.

Plasticizers that may be used in this invention include adipate, azelate, enzoate, citrate, stearate, isoebucate, sebacate, triethyl citrate, tri-nbutyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, acetyltributylcitrate, acetyltriethylcitrate, glycerin sorbitol, diethyloxalate, diethylmalate, diethylfbmarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 0.1% to about 20% of the plasticizer can be used. The addition of plasticizer should be approached with caution so as not to compromise the integrity of the gelatin capsule or cause leakage. In certain compositions it is better not to use plasticizers.

Examples of other additives that may be used as part of the formulations of the invention include, but are not limited to carbohydrates, sugars, sucrose, sorbitol, mannitol, zinc salts, tannic acid salts; salts of acids and bases such as sodium and potassium phosphates, sodium and potassium hydroxide, sodium and potassium carbonates and bicarbonates; acids such as hydrochloric acid, sulfuric acid, nitric acid, and phosphoric acid, citric acid, tartaric acid, and benzoic acid.

Materials such as the alkali metal chlorides, ammonium chloride, and chlorides of Ba, Mg, Ca, Cu, Fe and Al; alkali or alkaline earth solutions of acetates, nitrates, phosphates, and hydroxides may be used in this invention.

Hygroscopic or aqueous materials must be used with caution if at all. Limited quantities have been incorporated in certain compositions.

The composition of the invention containing one or more opioid agonist or narcotic analgesic or abuse-able substances may be made by any method wherein the quantity or ratio and type of clays, controlled release agents, oily, fatty or waxy substance and optionally fillers is sufficient to form a paste, liquid or semi solid matrix, magma of the entire composition. Preferably, the entire quantity of the composition is dissolved, dispersed, emulsified or suspended in the oily, fatty or waxy substances. Typically, the clays, controlled release agent and oily, fatty or waxy substances are combined, such as by blending or mixing under high shear until the clays, controlled release agent is completely dissolved, or homogeneous paste is formed. The components may be added separately one after the other. The narcotic agent is added under high shear to form a homogeneous non Newtonian, thixotropic or pseudoplastic paste or liquid/semi solid matrix. The order of incorporation depends on the outcome to be achieved. A cold process under room temperature conditions is preferred, however solid substances may be heated to their liquid state prior to incorporation. Alternatively, the composition may be processed in a jacketed vessel which allows precise control of the processing temperature. Other pharmaceutically acceptable additives, such as those described above, may be incorporated before, after, or during the addition of controlled release agents or narcortic analgesics.

EXAMPLE 1

Extended Release Oxycodone (Abuse Resistant and Alcohol Resistant Capsules)

| Component | Amount (% w/w) |
| --- | --- |
| Oxycodone | 20 |
| Corn Oil | 50 |
| Carbopol 971 | 8 |
| Hydroxypropylmethyl cellulose (METHOCEL ™ K100M Premium) | 22 |

The samples were prepared:
1) Weigh corn oil in a glass beaker and immerse Silverson high shear mixer fitted with a homogenizing head into the oil.
2) Gradually add carbopol followed by hydroxypropylmethyl cellulose while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules

EXAMPLE 2

Extended Release Oxycodone (Abuse Resistant and Alcohol Resistant Capsules)

| Component | Amount (% w/w) |
|---|---|
| Oxycodone | 20 |
| Corn Oil | 49 |
| Carbopol 971 | 8 |
| Bentonite | 1 |
| Hydroxypropylmethyl cellulose (METHOCEL ™ K100M Premium) | 22 |

The samples were prepared:
1) Weigh corn oil in a glass beaker and immerse Silverson high shear mixer fitted with a homogenizing head into the oil.
2) Gradually add bentonite, carbopol and hydroxypropylmethyl cellulose while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules

EXAMPLE 3

Extended Release Oxycodone (Abuse Resistant and Alcohol Resistant Capsules)

| Component | Amount (% w/w) |
|---|---|
| Oxycodone | 26 |
| Corn Oil | 49 |
| Sucrose acetate isobutyrate | 2 |
| Bentonite | 1 |
| Hydroxypropylmethyl cellulose (METHOCEL ™ K100M Premium) | 22 |

The samples were prepared:
1) Weigh Sucrose acetate isobutyrate and place in a glass beaker. Place beaker on a hot plate and heat until the Sucrose acetate isobutyrate becomes molten. Immerse Silverson high shear mixer fitted with a homogenizing head into the molten liquid and gradually add the oil under high shear.
2) Gradually add bentonite, and hydroxypropylmethyl cellulose while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules Extended Release Oxycodone (Abuse Resistant and Alcohol Resistant Capsules)

| Component | Amount (% w/w) |
|---|---|
| Oxycodone | 26 |
| Cotton seed oil | 45 |
| Carbopol 934 | 5 |
| Bees Wax | 3 |
| Bentonite | 1 |
| Hydroxypropylmethyl cellulose (METHOCEL ™ KI OOM Premium) | 20 |

The samples were prepared:
1) Weigh Bees Wax and place in a glass beaker. Place beaker on a hot plate and heat until the Bees Wax becomes molten. Immerse Silverson high shear mixer fitted with a homogenizing head into the molten liquid and gradually add the oil under high shear.
2) Gradually add bentonite, carbopol and hydroxypropylmethyl cellulose while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules

EXAMPLE 5

Extended Release Oxycodone (Abuse Resistant and Alcohol Resistant Capsules)

| Component | Amount (% w/w) |
|---|---|
| Oxycodone | 26 |
| Castor oil | 45 |
| Carbopol 934 | 5.5 |
| Polyethylene Glycol 8000 | 5 |
| Bentonite | 2.5 |
| Polyethylene Oxide WSR-303 | 16 |

The samples were prepared:
1) Weigh polyethylene glycol and place in a glass beaker. Place beaker on a hot plate and heat until the polyethylene glycol becomes molten. Immerse Silverson high shear mixer fitted with a homogenizing head into the molten liquid and gradually add the oil under high shear.
2) Gradually add bentonite, carbopol and polyethylene oxide while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules Extended Release Oxycodone (Abuse Resistant and Alcohol Resistant Capsules)

| Component | Amount (% w/w) |
| --- | --- |
| Oxycodone | 25 |
| Corn oil | 40 |
| Carbopol 934 | 8 |
| Sodium lauryl sulphate | 10 |
| Hydroxypropylmethyl cellulose (METHOCEL ™ K100M Premium) | 18 |

The samples were prepared:
1) Weigh the oil in a glass beaker. Immerse Silverson high shear mixer fitted with a homogenizing head into the oil.
2) Gradually add carbopol and hydroxypropylmethyl cellulose while stirring vigorously until a homogeneous blend is observed.
3) Add oxycodone gradually while stirring vigorously until a homogeneous blend is observed.
4) The result is a semi-solid or paste which can be filled into hard gelatin capsules without "stringing".
5) Take samples from top, middle and bottom to determine potency and homogeneity of the mix.
6) Fill into hard gelatin capsules Example 7

Combination Extended release Oxycodone+Immediate release Tramadol (Abuse resistant and alcohol resistant capsules) (i) Preparation of immediate release tramadol paste (Preparation 1)

| Component | Amount (% w/w) |
| --- | --- |
| Tramadol | 25 |
| Corn oil | 40 |
| Starch 1500 | 8 |
| Crospovidone | 5 |
| Hydroxypropylmethyl cellulose (METHOCEL ™ E5 Premium LV) | 18 |

(ii) Preparation of controlled release Oxycodone paste (Preparation 2) This is made as taught in Example 1.
(iii) Preparation of combination Extended release Oxycodone+Immediate release Tramadol (Abuse resistant and alcohol resistant capsules)
Fill the required amount of preparation 1 into the hard gelatin capsule followed by preparation 2. Seal the capsule.

In another embodiment a separation layer made of a wax such as carnuba wax or a high molecular weight poloyethylene glycol e.g., PEG 8000 may be filled into the capsule to separate two or preparations in situation incompatibility or cross migration of components is of concern. In this way several combinations of active substances are possible.

EXAMPLE 8

Film coated Abuse resistant and alcohol resistant capsules This consist of film coating capsules made in Example 1 with a polymethacrylate such as Eudragit L or S to impart a delayed or timed release characteristics or lag phase.

EXAMPLE 9

Film coated Abuse resistant and alcohol resistant capsules This consist of film coating capsules made in Example 1 with a cellulose ether such as ethylcellulose alone or in combination with water soluble polymers e.g., hydroxypropylmethyl cellulose.

EXAMPLE 9

Film coated Abuse resistant and alcohol resistant capsules This consist of film coating capsules made in Example 1 with a polymethacrylate such as Eudragit E to provide a protective sealing coat or moisture barrier or improve mechanical properties.

It should be understood that various modifications and ramifications of this basic invention will become apparent to those skilled in the art upon a reading of this disclosure. These are intended to be included within the scope of this invention. Also, substances can be added to this composition or can be used together in this composition; these also are contemplated to be included within the spirit of this invention. The present composition can be used alone without any supporting structure or can be used if desired with open faced grids, one face open structures, or completely closed structures. It can also be used in foams, sponges, walls, around pipes or can be deposited or sprayed onto any desired structure.

We claim:

1. A pharmaceutical composition comprising:
   (i) an active pharmaceutical agent selected from the group consisting of an opioid and an opiate; and
   (ii) 40-50% by weight of an oil selected form the group consisting of almond oil, canola oil, castor oil, corn oil, cottonseed oil, mineral oil, olive oil, olive-pomace oil, peanut oil, safflower oil, sesame oil, soybean oil, sunflower oil, and mixtures thereof; and
   (iii) at least 15% by weight of a controlled-release agent selected from the group consisting of hydroxypropyl methylcellulose (hypromellose), hydroxypropyl cellulose, and polyethylene oxide,
   wherein the composition is a non-aqueous paste.

2. The pharmaceutical composition of claim 1, wherein (1) the pharmaceutical composition further comprises a clay mineral and (2) the clay mineral is 0.5-20% by weight of the pharmaceutical composition.

3. The pharmaceutical composition of claim 2, wherein the clay mineral is bentonite.

4. The pharmaceutical composition of claim 3, wherein bentonite is 1.0-2.5% by weight of the pharmaceutical composition.

5. The pharmaceutical composition of claim 1, wherein the pharmaceutical composition further comprises bentonite.

6. The pharmaceutical composition of claim 1, wherein the controlled-release agent is hydroxypropyl methylcellulose (hypromellose).

7. The pharmaceutical composition of claim 6, wherein the hydroxypropyl methylcellulose (hypromellose) is 18-22% by weight of the pharmaceutical composition.

8. The pharmaceutical composition of claim 1, wherein the pharmaceutical composition further comprises a carbomer.

9. The pharmaceutical composition of claim 8, wherein the carbomer is 5-8% by weight of the pharmaceutical composition.

10. The pharmaceutical composition of claim 1, wherein the active pharmaceutical agent is an opioid selected from the group consisting of oxycodone and tramadol.

11. The pharmaceutical composition of claim 10, wherein the opioid is oxycodone.

12. The pharmaceutical composition of claim 1, wherein the pharmaceutical composition is on a structure.

13. The pharmaceutical composition of claim 12, wherein the structure is a transdermal patch.

14. A pharmaceutical composition comprising:
(i) an active pharmaceutical agent selected from the group consisting of an opioid and an opiate; and
(ii) 3-50% by weight of an oil selected form the group consisting of almond oil, canola oil, castor oil, corn oil, cottonseed oil, mineral oil, olive oil, olive-pomace oil, peanut oil, safflower oil, sesame oil, soybean oil, sunflower oil, and mixtures thereof; and
(iii) at least 15% by weight of a controlled-release agent selected from the group consisting of hydroxypropyl methylcellulose (hypromellose), hydroxypropyl cellulose, and polyethylene oxide; and
(iv) a carbomer, wherein the carbomer is at least 5% by weight of the pharmaceutical composition but less than or equal to 8% by weight of the pharmaceutical composition,
wherein the composition is a non-aqueous paste.

15. The pharmaceutical composition of claim 14, wherein (1) the pharmaceutical composition further comprises a clay mineral and (2) the clay mineral is 0.5-20% by weight of the pharmaceutical composition.

16. The pharmaceutical composition of claim 15, wherein the clay mineral is bentonite.

17. The pharmaceutical composition of claim 16, wherein bentonite is 1.0-2.5% by weight of the pharmaceutical composition.

18. The pharmaceutical composition of claim 14, wherein the pharmaceutical composition further comprises bentonite.

19. The pharmaceutical composition of claim 14, wherein the controlled-release agent is hydroxypropyl methylcellulose (hypromellose).

20. The pharmaceutical composition of claim 19, wherein the hydroxypropyl methylcellulose (hypromellose) is 18-22% by weight of the pharmaceutical composition.

21. The pharmaceutical composition of claim 14, wherein the carbomer is 8% by weight of the pharmaceutical composition.

22. The pharmaceutical composition of claim 14, wherein the active pharmaceutical agent is an opioid selected from the group consisting of oxycodone and tramadol.

23. The pharmaceutical composition of claim 22, wherein the opioid is oxycodone.

24. The pharmaceutical composition of claim 14, wherein the pharmaceutical composition is on a structure.

25. The pharmaceutical composition of claim 24, wherein the structure is a transdermal patch.

26. A pharmaceutical composition comprising:
(i) an active pharmaceutical agent selected from the group consisting of an opioid and an opiate; and
(ii) 40-50% by weight of an oil selected form the group consisting of almond oil, canola oil, castor oil, corn oil, cottonseed oil, mineral oil, olive oil, olive-pomace oil, peanut oil, safflower oil, sesame oil, soybean oil, sunflower oil, and mixtures thereof;
(iii) at least 15% by weight of a controlled-release agent comprising hydroxypropyl methylcellulose (hypromellose); and
(iv) 0.5-20% by weight of a clay mineral;
wherein the composition is a non-aqueous paste.

* * * * *